United States Patent [19]

Feld et al.

[11] 4,007,223
[45] Feb. 8, 1977

[54] METHOD OF PREPARING P-NITROBENZOIC ACID

[75] Inventors: Marcel Feld, Porz-Wahn; Hermann Richtzenhain, Much-Schwellenbach, both of Germany

[73] Assignee: Dynamit Nobel Aktiengesellschaft, Cologne, Germany

[22] Filed: Dec. 23, 1974

[21] Appl. No.: 535,862

[30] Foreign Application Priority Data

Dec. 29, 1973 Germany .......................... 2365131

[52] U.S. Cl. .......................................... 260/524 R
[51] Int. Cl.$^2$ ...................................... C07C 51/33
[58] Field of Search ............................... 260/524

[56] References Cited

UNITED STATES PATENTS 2,833,816  5/1958  Saffer et al. ..................... 250/524
3,665,030  5/1972  Radzizky et al. .................. 250/524

OTHER PUBLICATIONS

Fieser et al., "Reagents for Org. Syn.", Wiley & Sons Inc., N.Y., 1967, p. 154.

*Primary Examiner*—Lewis Gotts
*Assistant Examiner*—Cary Owens
*Attorney, Agent, or Firm*—Burgess, Dinklage & Sprung

[57] ABSTRACT

Process of preparing a not discolored p-nitrobenzoic acid by oxidation of p-nitrotoluene with oxygen, which comprises contacting the oxygen with the p-nitrotoluene in an acetic acid reaction medium and in the presence of a cobalt-containing and bromine-containing catalyst at a temperature of 80° to 150° C. The cobalt is present as a cobalt salt in the amount of 0.01 to 0.1 moles per mole of p-nitrotoluene, and the amount of acetic acid is 3 to 15 moles per mole p-nitrotoluene.

17 Claims, No Drawings

METHOD OF PREPARING P-NITROBENZOIC ACID

BACKGROUND

The present invention describes a method of preparing p-nitrobenzoic acid by the oxidation of p-nitrotoluene with oxygen or oxygen-containing gases under elevated pressure and temperatures between 80° and 150° C in a saturated aliphatic carboxylic acid as solvent and in the presence of cobalt salts and brominous compounds as catalysts.

Numerous processes are known in which methyl groups on an aryl nucleus are oxidized by means of oxygen in the liquid phase and in the presence of suitable catalysts to form carboxyl groups. Preferred catalysts are cobalt and manganese salts combined with brominous compounds. Whenever solvents appear to be necessary or desirable, it is mainly saturated aliphatic carboxylic acids that are employed for the purpose, preferably acetic acid.

Elevated temperatures are necessary for starting the oxidation reaction and for the achievement of good volume-time yields. Many known processes therefore operate at temperatures above 150° C and in some cases even above 200° C. The optimum reaction conditions depend greatly on the structure and chemical properties of the substance that is to be oxidized. The oxidizability of the methyl group in toluene is thus considerably affected by the introduction of additional substituents in the nucleus.

The nitro group has been shown to cause difficulty in the oxidation (N. Ohta and T. Tezuka, Rept. Govt. Chem. Ind. Research Inst., Tokyo 51, 249–52 (1956); C.A. 51, 281 (1957)). The oxidation of nitrotoluene therefore requires higher reaction temperatures than the oxidation of toluene itself.

On the other hand, in technical oxidation processes low reaction temperatures are desired, for the purpose of suppressing undesired secondary reactions, and if acid solvents are used, the reactor material must satisfy stringent corrosion-resistance requirements. Precisely when acetic acid is used as a solvent, the high-alloy steels often used as vessel material are subject, in the presence of brominous compounds under oxidizing conditions, to corrosion which increases greatly as the temperature increases.

One of the undesirable secondary reactions promoted by high reaction temperatures in the air oxidation of alkyl aromatics is especially the total oxidation of starting product and/or solvent, that is, the oxidative decomposition of these products ultimately to water and carbon dioxide. In the case of acetic acid, for example, in the absence of other oxidizable substances, when air is passed through the solution under elevated pressure, an oxygen absorption is observed beginning at about 150° C and increasing greatly as the temperature rises, which is catalyzed by cobalt acetate, and is simultaneously accompanied by the formation of carbon dioxide and water.

Lastly, when air is passed through an acetic acid reaction solution, increasing amounts of entrained acetic acid vapors are observed as the reaction temperatures increase. The vapor pressure of acetic acid, at about 7.6 atmospheres at 200° C, amounts to three times what it is at 150° C (approx. 2.4 atmospheres). On this basis, at 200° C and at a pressure of 30 atmospheres, the vapor phase will contain approximately 25% acetic acid by volume, as compared with about 8% by volume at 150° C. The separation of the acetic acid from the residual air thus requires a technical expenditure that will be all the greater as the temperature of the reaction solution is higher, for the same working pressure.

From the viewpoints set forth above, the process for the oxidation of p-nitrotoluene according to U.S. Pat. No. 3,030,414, which delivers a yield of 86% p-nitrobenzoic acid at reaction temperatures of 150° to 250° C does not appear to be an optimum one, all the more so because the recommended inclusion of manganese salts as catalysts always results in a greatly discolored reaction product whose discoloration cannot be corrected even by repeated recrystallization from glacial acetic acid. In view of the preferred use of nitrobenzoic acid as a valuable starting product for a number of pharmaceutically useful substances, however, high purity is especially desirable, and a product that is not discolored is demanded.

THE INVENTION

The object of the present invention is thus an improved method of preparing p-nitrobenzoic acid with less discoloration of the product and a better yield. The conditions of the reaction are to reduce the corrosion of the reactor material, diminish the energy costs, preclude insofar as possible any total oxidation of starting product and/or solvent, and facilitate the condensation of acetic acid from the vapor phase.

The inclusion of manganese salts as catalysts has been recognized as a cause of great product discoloration. In the method of the invention the use of oxidation-promoting manganese salts is avoided, and only cobalt salts are used in addition to brominous compounds as catalysts. In this manner the p-nitrobenzoic acid is obtained in the form of flake-like, pale yellow crystals.

A solution of 1 gram of p-nitrobenzoic acid obtained in this manner, in 10 g of dimethylsulfoxide, will have an iodine color number of 2 to 3 on the iodine color scale of DIN Standard 6162. In comparison, a similar solution of a product obtained under comparable reaction conditions in the simultaneous presence of manganese salts will have an iodine color number of 40 on the same color scale.

The achievement of the required mild reaction conditions was based on the surprising observation that, under otherwise identical reaction conditions, there is a marked connection, within a certain range, between the starting temperature of the oxidation on the one hand and the concentration and composition of the catalyst on the other, the starting temperature of the reaction being manifested both by an abrupt increase in the rate of the temperature rise of the reaction solution and in an abrupt decrease of the oxygen content in the exhaust air leaving the reaction vessle, which can be detected by means of a measuring apparatus.

Cobalt compounds which are soluble in acetic acid serve as catalysts, examples being cobalt acetate, cobalt acetylacetonate, cobalt naphthenate, cobalt bromide, and others, combined, if desired, with lesser amounts of cobalt chloride, cobalt sulfate or cobalt nitrate, which have a lower solubility in acetic acid. The brominous compounds are particularly potassium, sodium and ammonium bromide, in addition to hydrogen bromide and elemental bromine, as well as other compounds supplying bromine ions. The quantity of the bromine compounds will amount generally to from 0,1 to 2,0 mol per mol of the cobalt compounds.

The acetic acid can be used as the solvent in anhydrous form, as glacial acetic acid, or as an aqueous solution of more than 90 wt.-%, preferably more than 95 wt.-% acetic acid. The amount of water present should not exceed 10, preferably 5 wt.% of the acetic acid.

To illustrate the relationship between the start-up temperature and the catalyst concentration, Table I lists the observed start-up temperatures in the p-nitrotoleune oxidations described in Examples 1 to 14 for the various molar ratios of p-nitroleune to cobalt (II) acetate tetrahydrate or cobalt (II) bromide hexahydrate.

diate products contained in solution in the mother liquor are thus recycled.

If the mother liquor were recycled directly together with the water the oxidation would stop after a few batches. Therefore, the reaction water has to be separated from the mother liquor. This can be accomplished without difficulty by fractional distillation or by azeotropic removal by means of a dewatering agent. Benzene and 1,2-dichloroethane have been used successfully as dewatering agents.

The quantity of the reaction water separated is an indication of any undesirable total oxidation that may have occurred during the reaction.

Thus, in the experimental series of Example 15, involving reaction temperatures from 180° to 200° C and Table I

| Example | Glacial acetic acid | Cobalt acetate | Cobalt bromide | p-nitro benzoic acid | Start-up temperature of the reaction |
|---|---|---|---|---|---|
| | Moles per mole of -nitrotoluene | | | % of the theory | |
| 1 | 11 | 0.0046 | | 45 | 170 |
| 2 | 11 | 0.0092 | | 84 | 160 |
| 3 | 11 | 0.0137 | | 87.5 | 145 |
| 4 | 11 | 0.0183 | | 90.5 | 135 |
| 5 | 11 | 0.0275 | | 90.5 | 120 |
| 6 | 11 | 0.0366 | | 91.5 | 115 |
| 7 | 11 | 0.0458 | | 90.5 | 100 |
| 8 | 10 | 0.0458 | | 93 | 95 |
| 9 | 6.7 | 0.0458 | | 92 | 90 |
| 10 | 19 | 0.0275 | | 86.5 | 165 |
| 11 | 10 | | 0.014 | (no reaction up to 148) | |
| 12 | 10 | | 0.021 | 97.5 | 140 |
| 13 | 10 | | 0.035 | 88 | 135 |
| 14 | 10 | | 0.059 | 84 | 130 |

The yields of p-nitrobenzoic acid which are also listed in Table I refer to the product isolated directly from the reaction mixture and refined by washing. In other words, the figures do not include amounts still contained in mother liquor and washing solutions. If these are included, the total yield for Example 8 is increased to 99%, for example.

Examples 8 and 9 differ from one another and from Example 7, for the same ratio of p-nitrotoluene to cobalt acetate, in the degree of dilution of the starting solution. These examples show that the start-up temperature of the reaction also depends on the concentration of the solution to such an extent that an increase in the starting concentration of p-nitrotoluene will enable the start-up temperature to be lower for the same molar ratio of p-nitrotoluene to catalyst. Comparison of Examples 5 and 10 confirms this observation.

On the basis of the observations described, it is possible, therefore, to prepare non-discolored p-nitrobenzoic acid in a high yield under relatively mild reaction conditions. Although these advantages justify the use of the necessary high cobalt salt concentrations of 0.01 to 0.1 mole per mole of p-nitrotoluene, the re-use of the cobalt salts is desirable.

The mother liquor containing the catalyst after the product and the water of reaction has been removed can be re-used repeatedly as solvent for additional oxidations of p-nitrotoluene without any impairment of the process. The addition of fresh cobalt salts is unnecessary, so that not only is is possible to achieve the desirable re-use of the catalyst, but also to achieve an increase in the total yield of p-nitrobenzoic acid, because the end products, starting products and intermefour recyclings of the mother liquor, the water amounted to 170% of the quantity that was to be expected in the case of a quantitative reaction of the p-nitrotoluene, including the water content of the catalyst. For a total yield of 90.5% of p-nitrobenzoic acid, this indicates a considerable amount of total oxidation, especially of the solvent. A second set of experiments (Examples 16) at a reaction temperature of 130° C and two recyclings of the mother liquor, the amount of water separated was 99.5% of the amount corresponding to a complete reaction of the p-nitrotoluene. The total yield of p-nitrobenzoic acid amounted to 95.5% of the theory, not including the acid remaining in solution in the mother liquor of the third experiment of this series. Thus, at the relatively low reaction temperature of 130° C, no detectable total oxidation of solvent and-/or starting product takes place.

In the case of the series of 5 experiments decribed in Example 15, the cobalt content was reduced to <0,25 percent by weight based on the weight of p-nitro-toluene, by recycling the mother liquor. There is no reason why further, repeated recycling of the mother liquor cannot be performed.

The method of the invention thus makes it possible, by the use of cobalt salt concentrations of 0.01 to 0.1, preferably 0.02 to 0.08, and especially 0.02 to 0.06 mole per mole of the initially present p-nitrotoluene, and by the use of 3 to 15, and preferably 5 to 8, moles of acetic acid, to produce non-discolored p-nitrobenzoic acid at technically desirable, low reaction temperatures of 80° to 150° C. In the case of cobalt bromide, at least 0.02 mole is desirable per mole of p-nitrotoluene. By recycling the mother liquor after separation of the end product and reaction water, the total yield of p-nitrobenzoic acid can be increased to more than 95%, and the catalyst consumption can be reduced to an economically reasonable value of less than 0.01 mole of cobalt salt per mole of reacted p-nitrotoluene.

The process can be performed continuously or discontinuously.

SUMMARY

Thus the invention provides a preparing a not discoloured p-nitrobenzoic acid by oxidation of p-nitrotoluene with oxygen, which comprises contacting the oxygen with the p-nitrotoluene in an acetic acid reaction medium and in the presence of a cobalt-containing and bromine-containing catalyst for the oxidation, at a temperature of 80° to 150° C. The cobalt is present as a cobalt salt in the amount of 0.01 to 0.1 moles per mole of p-nitrotoluene, and the amount of acetic acid is 3 to 15 moles per mole p-nitrotoluene.

EXAMPLES

The reaction vessel was an enameled 4-liter stirring autoclave with a feeding tube and a reflux condenser. After the substances were charged into the vessel, a pressure of 30 atmospheres was established in the vessel by feeding compressed air through it with a rate of emergence of 5 to 8 liters per minute, and the contents were heated with strong stirring. The oxygen content of the emerging residual gas was measured by means of a "Servomex" Analyzer Model OA 250 (Mfr.: Servomex Controls Ltd.). At the end of the reaction the mixture was cooled down to room temperature, the precipitated reaction product was filtered out, successively washed with 700 ml of glacial acetic acid and 3 liters of water, and vacuum-dried at 100° C.

EXAMPLES 1 to 7

(Examples for purposes of comparison):

600 g of p-nitrotoluene were oxidized in 2700 ml of glacial acetic acid by the method described above, in the presence of 8 g of KBr and amounts of 5 g, 10 g, 15 g, 20 g, 30 g, 40 g and 50 g of cobalt(II) acetate tetrahydrate in Examples 1 to 7, respectively. The reaction temperature was increased to 180° to 200° C after the start-up temperature was reached, and then held constant until the absorption of oxygen had ceased. The start-up temperatures and yields of the p-nitrobenzoic acid identified by the infrared spectrum are to be found in Table I.

EXAMPLE 8

With the addition of 8 g KBr and 50 g $Co(OAc)_2 \cdot 4H_2O$, 600 grams of p-nitrotoluene was oxidized in 2500 ml of glacial acetic acid at a reaction temperature of 120° C. The absorption of oxygen began at 95° C and ended 3 hours later. While the minimum oxygen content in the residual gas was determined to be 3.6%, qualitative testing for $CO_2$ remained negative. 681 g of p-nitrobenzoic acid (93% of the theory) was isolated from the reaction mixture, with a neutralization equivalent of 167.5 and a melting point of 239° C. An additional 45 g of p-nitrobenzoic acid was found acidimetrically in the residue obtained by concentrating the mother liquor (total yield 99% of the theory).

A solution of 1 g of reaction product in 10 g of dimethylsulfoxide has a value of 2–3 on the iodine color scale of DIN 6162.

EXAMPLE 9

900 g of p-nitrotoluene was oxidized in 2500 ml of glacial acetic acid after the addition of 75 g of $Co(OAc)_2 \cdot 4H_2O$ and 12 g KBr at a reduction temperature of 120° C (startup temperature 90° C) and a reaction time of 4 hours. 1012.5 grams of p-nitrobenzoic acid (92% of the theory) was filtered from the reaction mixture, and then, after the addition of 500 ml of benzene, 137 g of water (101% of the theory) was separated by azeotropic distillation.

EXAMPLE 10

(For purposes of comparison)

The oxidation of 300 g of p-nitrotoluene in 2500 ml of glacial acetic acid, in the presence of 4 g KBr and 15 g $Co(OA)_2 \cdot 4H_2O$, at a reaction temperature of 185° C and a reaction time of 3 hours, gave a yield of 86.5% of p-nitrobenzoic acid. The absorption of oxygen began at 165° C. During the reaction $CO_2$ was detected qualitatively in the residual gas. After the addition of 500 ml of benzene, 103 g of water (240% of the theory) was distilled azeotropically from the mother liquor.

EXAMPLES 11 to 14

With amounts of 20 g, 30 g, 50 g and 85 g of $CoBr_2 \cdot 6H_2O$ in Examples 11 to 14, respectively, the oxidation of 600 g of p-nitrotoluene in 2500 ml of glacial acetic acid was performed in the usual manner at a reaction temperature of 145° C. In the case of Example 11, no absorption of oxygen was observed up to a temperature of 148° C. For the rest of the Examples, the yields of p-nitrobenzoic acid and the observed start-up temperatures are listed in Table I.

EXAMPLE 15

(Example for purposes of comparison)

600 of p-nitrotoluene was oxidized in 2700 ml of glacial acetic acid after the addition of 8 g KBr and 30 g $Co(OAc)_2 \cdot 4H_2O$. The reaction product was suction filtered, washed and dried. The mother liquor was combined with the glacial acetic acid used for washing, and after the addition of 500 ml of benzene, the water was separated azeotropically. Benzene and excess acetic acid were removed by distillation down to a remainder of 2500 ml. After the addition of 600 g of p-nitrotoluene, the oxidation was performed again and the product was processed as before. The same procedure was repeated three more times. At reaction temperatures of 180° C, the oxidation of the total input amount of 3000 g of p-nitrotoluene gave a yield of 3313 g of p-nitrobenzoic acid (90.5% of the theory), 689 g of water having been removed (170% of the theory).

EXAMPLE 16

In the presence of 40 g of $Co(OAc)_2 \cdot 4H_2O$ and 8 g of KBr, 600 grams of p-nitrotoluene was oxidized in 2500 ml of glacial acetic acid. The product was processed as in the above Example 15; after the addition of 600 more grams of p-nitrotoluene, the oxidation was performed again, and the procedure was repeated one more time. The reaction temperature in all three procedures was not increased above 130° C. Filtration of the 3 reaction solutions yielded 2096 grams of p-nitrobenzoic acid (95.5% of the theory). After the addition to the mother liquors of 400 ml of 1,2-dichloroethane for each batch, 247 grams of water (99.5% of the theory) were removed by azeotropic distillation.

EXAMPLE 17

(For purposes of comparison)

750 g of p-nitrotoluene was oxidized in 2250 ml of glacial acetic acid, after the addition of 15 g of $NH_4Br$, 4.5 g of $Co(OAc)_2 \cdot 4H_2O$ and 4.5 g of $Mn(OAc)_2 \cdot 4H_2O$, at a reaction temperature of 175° C. The reaction product was washed and dried as before. 795 g (87% of the theory) of brown-discolored p-nitrobenzoic acid was obtained, having a melting point of 235°–36° C. The solution of 1 g of the product in 10 g of dimethylsulfoxide has a value of 40 on the iodine color scale. After recrystallization three times from glacial acetic acid, the melting point was 237°–40° C, while the iodine number remained unchanged.

What is claimed is:

1. Process of preparing p-nitrobenzoic acid of high purity by oxidation of p-nitrotoluene with oxygen, which comprises contacting the oxygen with the p-nitrotoluene in an acetic acid reaction medium and in the presence of a cobalt-containing and bromine-containing catalyst for the oxidation, at a temperature of 80° to 150° C for a time sufficient for the oxidation, the cobalt being present as a cobalt salt in the amount of 0.01 to 0.1 moles per mole of p-nitrotoluene, and the amount of acetic acid being 3 to 15 moles per mole p-nitrotoluene.

2. Process of claim 1, wherein the amount of cobalt salt is 0.02 to 0.08 moles per mole of p-nitrotoluene.

3. Process of claim 1, wherein the amount of cobalt salt is 0.02 to 0.06 moles per mole of p-nitrotoluene.

4. Process of claim 1, wherein the amount of acetic acid is 4 to 6 moles per mole of p-nitrotoluene.

5. Process of claim 3, wherein the amount of acetic acid is 4 to 6 moles per mole of p-nitrotoluene.

6. Process of claim 1, wherein following said contacting, the p-nitrobenzoic acid is removed from the acetic acid reaction medium and the reaction medium containing said catalyst is re-used as reaction medium for the oxidation of additional p-nitrotoluene.

7. Process of claim 1, wherein the acetic acid is glacial acetic acid.

8. Process of claim 1, wherein cobalt bromide is used as the catalyst.

9. Process of claim 1, wherein said salt is cobalt acetate.

10. Process of claim 6, wherein water is produced in the reaction in the reaction medium, and water is removed from the reaction medium, azeotropically employing a water removal agent, before said re-use.

11. Process of claim 10, wherein the water removal agent is benzene or 1,2-dichloroethane.

12. Process of claim 1, wherein the cobalt-containing catalyst is a cobalt compound soluble in acetic acid, and the bromine-containing catalyst is of the group potassium bromide, sodium bromide, ammonium bromide, hydrogen bromide and elemental bromine.

13. Process of claim 1, wherein the cobalt-containing catalyst is of the group cobalt acetate, cobalt acetylacetonate, cobalt naphthenate, and cobalt bromide, and the bromine-containing catalyst is of the group potassium bromide, sodium bromide, ammonium bromide, hydrogen bromide and elemental bromine.

14. Process of claim 1, wherein the cobalt of the cobalt-containing catalyst is cobalt (II).

15. Process of claim 1, wherein said medium is free of manganese salt.

16. Process of claim 1, wherein the iodine color number of the product is 2 to 3.

17. Process of claim 14, wherein said medium is free of manganese salt.

* * * * *

UNITED STATES PATENT AND TRADEMARK OFFICE
CERTIFICATE OF CORRECTION

PATENT NO. : 4,007,223
DATED : February 8, 1977
INVENTOR(S) : Dr. Marcel Feld and Dr. Hermann Richtzenhain It is certified that error appears in the above-identified patent and that said Letters Patent are hereby corrected as shown below:

Column 2, line 57, change "vessle" to --vessel--.

Column 6, line 5, change "reduction" to --reaction--.

Signed and Sealed this

Twenty-fourth Day of May 1977

[SEAL]

Attest:

RUTH C. MASON
*Attesting Officer*

C. MARSHALL DANN
*Commissioner of Patents and Trademarks*